United States Patent [19]

Weiner et al.

[11] Patent Number: 5,587,313
[45] Date of Patent: Dec. 24, 1996

[54] METHOD FOR FERMENTATION OF MARINE BACTERIA

[75] Inventors: Ronald M. Weiner, Adelphi; David M. Manyak, Annapolis, both of Md.

[73] Assignee: University of Maryland, College Park, Md.

[21] Appl. No.: 402,480

[22] Filed: Mar. 10, 1995

[51] Int. Cl.$^6$ .............................. C12N 1/00; C12N 1/12; C12N 1/20
[52] U.S. Cl. ...................... 435/252.1; 424/93.4; 435/243
[58] Field of Search ................................ 435/243, 252.1; 424/93.4

[56] References Cited

PUBLICATIONS

Rebecca A. Devine and Ronald M. Weiner, "Hyphomonas species metabolise amino acids using Krebs cycle enzymes" *Microbios* (1990) 62:137–153.

David M. Manyak and Ronald M. Weiner, "Fermentation of Marine Bacteria for Production of Novel Biomaterials" *Manual of Industrial Microbiology & Biotechnology* ed. by Demayne & Solomon. ASM (1986).

Thomas L. Miller and Bruce W. Churchill, "Substrates for Large–Scale Fermentations" *Abstr. Am. Chem. Soc.* (1994) Chapter 10, 122–136.

*Primary Examiner*—John W. Rollins
*Assistant Examiner*—Deborah K. Ware
*Attorney, Agent, or Firm*—Watson Cole Stevens Davis, P.L.L.C.

[57] ABSTRACT

We have developed methods for low-cost fermentation of marine bacteria. A cost- and performance-optimized culture medium containing liver digest and suitable salts was developed and compared to currently available culture media. Cell counts as high as $10^2$/ml were achieved, and growth was supported for a variety of marine strains tested to date. Large scale fermentation of marine bacteria is a promising approach for producing commercially valuable biopolymers for industrial applications.

9 Claims, No Drawings

METHOD FOR FERMENTATION OF MARINE BACTERIA

BACKGROUND OF THE INVENTION

1. Field of the Invention

This invention relates generally to a method for achieving large-scale, low-cost fermentation of marine bacteria. More specifically, this invention relates to a cost and performance-optimized culture medium for marine bacteria.

2. Description of the Related Art

Marine organisms, including marine bacteria, produce a variety of polymeric biomaterials having unique properties and potential industrial applications. As with other natural biopolymers, a major hurdle to commercializing these materials is the availability of a renewable supply of raw materials at sufficiently low cost. The inventors have been developing adhesive polymers from benthic marine bacteria that bond to wetted surfaces underwater. The biofilms that these bacteria produce consist of exopolysaccharides (EPS), some with integral peptide residues.

In attempting to harvest products from marine bacteria, it was noted that the costs were prohibitive, since experimental media such as Marine Broth 2246 and Brain Heart Infusion were more than $60/lb. and over 30 grams were required to prepare a liter of medium. Therefore, in view of the aforementioned deficiencies attendant with prior art methods of large-scale culture of marine bacteria, it should be apparent that there still exists a need in the art for a high-quality, low-cost commercial medium for the growth of marine bacteria that would also allow the organism to produce the required product.

SUMMARY OF THE INVENTION

Accordingly, a major object of the present invention is to provide a method of achieving large-scale, low cost fermentation of marine bacteria.

In general, this invention relates to a cost and performance-optimized culture medium for large-scale fermentation of marine bacteria.

A further aspect of this invention is a large-scale fermentation method for marine bacteria using the culture medium of the present invention.

With the foregoing and other objects, advantages, and features of the invention that will become hereinafter apparent, the nature of the invention may be more clearly understood by reference to the following detailed description of the preferred embodiments of the invention and to the appended claims.

DETAILED DESCRIPTION OF THE PREFERRED EMBODIMENTS OF THE INVENTION

This invention arose from a desire of the inventors to develop an improved method of culturing marine bacteria. More specifically, the inventors sought to provide a low-cost, high-quality culture medium capable of supporting commercially useful quantities of many species of marine bacteria.

It is generally known in the art that marine bacteria require a specialized environment in order to be maintained in culture. Currently available culture media, such as Marine Broth 2246 or Brain Heart Infusion are adequate for culturing small quantities of certain marine bacteria. However, their high cost and incompatibility with a broad range of marine bacterial species has made large-scale commercial culture of marine bacteria impractical.

Surprisingly, the present inventors have developed methods for low-cost fermentation of marine bacteria in order to scale up production of exopolysaccharaides. A cost and performance-optimized culture medium was selected from among several dozen media which were considered by the present inventors. This culture medium was unexpectedly superior to any known culture medium. Cell counts as high as $10^{12}$/ml were achieved, and growth was supported for a variety of marine strains tested to date. Large scale fermentation of marine bacteria is a promising approach for producing commercially valuable biopolymers for industrial applications.

The inventors have found that a culture medium comprising liver digest (LD) and appropriate mineral salts provides an inexpensive, high-quality medium which is capable of supporting large quantities of many species of marine bacteria. The culture medium of the present invention provides for optimal growth and maintenance (i.e., continuing viability) of marine bacteria in culture.

Besides its lower cost (e.g., $1/100-1/1000$ the cost of currently available media) LD also supports a greater diversity of marine bacteria than conventional media, and supports production of products such as exopolysaccharides (EPS), enzymes (proteinase and para-hydroxy-phenyl pyruvate hydroxylase) and melanin pigment.

Liver digest is a high quality animal protein derived from fresh whole livers, which are preferably porcine, bovine, or ovine livers, most preferably porcine livers. Liver digest is well known to those skilled in the art. Any liver digest is useful in the practice of the present invention. Many brands of liver digest are currently available. An example of a suitable liver digest is Spray Dried Liver (available from American Protein Corporation of Ames, Iowa). This is a porcine liver product which typically contains 65% protein, >13% fat, 3.82 mg/g cholesterol, and 1.1% phosphorous. This product contains all of the amino acids necessary for growth and maintenance of cultured marine bacteria, and typically contains more than 10% w/v glutamic acid, more than 5% w/v aspartic acid and leucine, from 3–5% w/v serine, proline, alanine, valine, arginine, threonine, glycine, and lysine, and less than 3% w/v isoleucine, tyrosine, hydroxylysine, tryptophan, cystine, methionine, phenylalanine, and histidine. The LD of the culture medium of the present invention is present in an amount sufficient for the growth and maintenance of marine bacteria, preferably from 1–5% liver digest wt/vol, more preferably from 2–4% wt/vol, most preferably 3% wt/vol.

By "growth" of marine bacteria, applicants mean that the culture medium of the present invention will support increases in density of marine bacteria. To those skilled in the art this generally means increases in cell density to high cell counts. In the case of the present invention such cell counts may exceed $10^{12}$ cells/ml. By "maintenance" of marine bacteria, applicants mean that the culture medium of the present invention will support a viable static population density of marine bacteria, typically for periods of more than 48 hours, in many cases more than 70 hours.

A wide variety of bacteria are considered to be marine bacteria. Such bacteria include, but are not limited to, species of bacteria from the genera *Acinetobacter, Aeromonas, Alteromonas, Hyphomonas, Pseudomonas, Shewanella, Vibrio,* and *Hyphomonas.*

The culture medium of the present invention also may contain NaCl in a concentration of 60–100 g/l, more preferably 70–90 g/l, most preferably 80 g/l. The culture medium of the present invention also may contain $MgCl \cdot 6H_2O$ in a concentration of 8.0–9.0 g/l, more preferably 8.5–9.0 g/l, most preferably 8.8 g/l. The culture medium of the present invention also may contain $Na_2SO_4$ in a concentration of 2.5–3.5 g/l, more preferably 3.0–3.3 g/l, most preferably 3.14 g/l. The culture medium of the present invention also may contain $NaHCO_3$ in a concentration of 0.01–0.30 g/l, more preferably 0.1–0.2 g/l, most preferably 0.16 g/l. The culture medium of the present invention also may contain KBr in a concentration of 0.01–0.20 g/l, more preferably 0.5–0.15 g/l, most preferably 0.08 g/l. The culture medium of the present invention also may contain $H_3BO_3$ in a concentration of 0.01–0.03 g/l, more preferably 0.015–0.025 g/l, most preferably 0.02 g/l. The culture medium of the present invention also may contain $SrCl_3$ in a concentration of 0.01–0.05 g/l, more preferably 0.02–0.04 g/l, most preferably 0.03 g/l. The culture medium of the present invention also may contain $NaSiO_3 \bullet 9H_2O$ in a concentration of 0.001–0.1 g/l, more preferably 0.005–0.05 g/l, most preferably 0.01 g/l. The culture medium of the present invention also may contain $NH_4NO_3$ in a concentration of 0.005–0.5 g/l, more preferably 0.01–0.1 g/l, most preferably 0.05 g/l. The culture medium of the present invention also may contain $FeCl_3 \bullet 6H_2O$ in a concentration of 0.005–0.5 g/l, more preferably 0.01–0.1 g/l, most preferably 0.05 g/l.

The culture medium of the present invention also may optionally contain $KH_2PO_4$ in a concentration of 5–20 g/l, more preferably 10–15 g/l, most preferably 13.6 g/l. The culture medium of the present invention also may optionally contain $K_2HPO_4$ in a concentration of 10–30 g/l, more preferably 15–25 g/l, most preferably 21.3 g/l.

The liver digest and salts of the present invention may be combined in any manner. The liver digest, and salts, may be dissolved or suspended in a liquid solvent. Preferably, the liver digest and salts are dissolved or suspended in water, more preferably distilled water, most preferably sterile distilled water. The pH of the solution or suspension is preferably corrected to fall within the approximate range of 7.0–8.0, more preferably to 7.25–7.75, most preferably to 7.5.

Having now generally described this invention, the same will be better understood by reference to certain specific examples, which are included herein for purposes of illustration only and are not intended to be limiting of the invention or any embodiment thereof, unless so specified.

EXAMPLE 1

COMPARISON OF COST AND EFFECTIVENESS OF VARIOUS COMMERCIAL MEDIA

In this experiment, the growth of two typical strains of marine bacteria, *Hyphomonas* and *Shewanella*, were compared. Table 1 (below) shows that only Fish Solubles and LD media were successful in cultivating these typical marine genera. The other commercial media did not support the growth of marine Genera.

TABLE 1

GROWTH OF TWO INDICATOR STRAINS ON VARIOUS COMMERCIAL NUTRIENT PRODUCTS

| NAME | COMPOSITION | APPROXIMATE COST ($/lb.) | MHS3 GROWTH | LSTD GROWTH |
|---|---|---|---|---|
| AP 100 | Pork stock | 1.00 | – | ++ |
| AP 300 | Whole blood | 0.45 | – | – |
| AP 620 | Dried blood plasma | 1.70 | – | – |
| AP 8000 | Whey protein | 0.90 | – | – |
| BEEF STOCK | | 1.25 | – | – |
| BHI (> 1%) | Bovine brain, heart | 48.00 | +++ | ++ |
| CATFISH 35 | | 0.25 | – | + |
| EXSL 440 | Extruded salmon | 0.39 | – | – |
| EXTR 400 | Extruded trout | 0.26 | – | – |
| FISH CONDENSATE | | 0.30 | – | – |
| FISH MEAL | | 0.30 | – | – |
| FISH SOLUBLES | | 0.45 | ++ | – |
| FISH STARTER | | 0.46 | –/+ | + |
| LIVER DIGEST | Porcine liver | 1.75 | ++++ | ++++ |
| MARINE (> 1%) | Peptone, salts | 55.00 | ++++ | ++++ |
| MICROBIOTONE | Peptones | 6.50 | – | – |
| OATS | | 0.50 | | |
| PHARMATONE | Peptones | 4.75 | – | – |
| POTATO + PHARMATONE | | 9.96 | – | – |
| PROFLO POWDER | Cottonseed powder | 0.29 | +/– | +/– |
| PROTEIN HYDROLYSATE | Collagen lysates | 2.50 | – | – |
| PROTEOSE | Peptones | 19.25 | – | – |
| SHRIMP GROWER | | 0.39 | | |
| SOFT MOIST SALMON | | 0.79 | – | – |
| SOY FLOUR | | 10.26 | – | – |
| TECHNICAL GELATIN | | 1.35 | – | – |
| TORUTEIN 10 | Yeast extracts | 2.35 | – | ++ |
| ZYEST FM | Yeast extracts | 2.20 | – | – |
| ZYEST 70 | Yeast extracts | 2.50 | – | – |

– no growth;
+ sparse growth;
++ growth;
++++ lavish growth

EXAMPLE 2

COMPARISON OF LIVER DIGEST AND MARINE BROTH 2216

In these experiments, the growth of selected species of marine bacteria on liver digest (LD) and Marine Broth 2216 (MB) were compared. Bacterial cultures were incubated for eight days at 25° C. The results of these experiments are presented in Table 2, below.

TABLE 2

| Microorganism | Growth | |
|---|---|---|
| | LD | MB |
| Acinetobacter calcoaceticus | +++ | +++ |
| Aeromonas cavie | +++ | +++ |
| A. hydrophila | +++ | +++ |
| A. veroni | +++ | +++ |
| Alteromonas haloplanktis | +++ | ++ |
| A. macleodii | +++ | + |
| A. nigrifaciens | ++ | ++ |
| A. putrefaciens | ++ | ++ |
| CB 1 | ++ | ++ |
| CB 2 | ++ | ++ |
| CB 3 | +++ | +++ |
| CB 4 | +++ | +++ |
| CB 5 | − | +++ |
| CB 6 | +++ | +++ |
| Hyphomonas MHS-2 | +++ | + |
| H. MHS-3 | +++ | +++ |
| H. neptunium | + | ++ |
| H. polmorpha smooth | + | ++ |
| H. VP-3 | +++ | +++ |
| H. VP-5 | ++ | ++ |
| H. VP-6 | − | +++ |
| Pseudomonas atlantica | ++ | ++ |
| P. enalia | ++ | ++ |
| P. fluorescens | ++ | ++ |
| Shewanella colwelliana (D) | +++ | +++ |
| S. colwelliana (S) | ++ | ++ |
| S. colwelliana (W) | +++ | +++ |
| Vibrio cholerae | +++ | +++ |
| V. fischeri | +++ | +++ |
| V. vulnificus | +++ | +++ |
| Xanthomonas campestris | ++ | ++ |

− no growth;
+ sparse growth;
++ growth;
+++ lavish growth

EXAMPLE 3

COMPARISON OF CELL DENSITIES OF SUSPENDED CULTURES IN LIVER DIGEST AND MARINE BROTH

Besides its lower cost (e.g., 1/100–1/1000 the cost of currently available media) LD also supports a greater diversity of bacteria than conventional media, and supports production of products such as exopolysaccharides (EPS), enzymes (proteinase and para-hydroxy-phenyl pyruvate hydroxylase) and melanin pigment.

This experiment was done by streaking the listed species on MB prepared with 1.5% Bacto agar (MA). Fermentation temperature was 25° C. The agitation impeller was set at 200 RPM. The aleration rate was 4 LPM. In MB, *Shewanella* achieved $10^9$–$10^{10}$ cells/ml. In LD densities ranged from $5\times10^{10}$–$1\times10^{11}$/ml. For *Hyphomonas* MHS-3, final cell densities were $2\times10^9$ in MB but $1$–$9\times10^{10}$ in LD. Thus LD supports approximately 1–2 orders of magnitude higher cell densities than MB at a 1/10–1/100 the cost (See Table 3). In large-scale fermentations ranging from 14–30 L (New Brunswick), LD supported greater cell densities than MB (See also Table 2, *A. macleodii* and *Hyphomonas* MHS-2).

TABLE 3

| MEDIUM | FINAL CELL DENSITY (cells/ml) | COST TO PRODUCE EPS ($/g) |
|---|---|---|
| MARINE BROTH | $3 \times 10^{10}$ | 988 |
| LIVER DIGEST | $1 \times 10^{12}$ | 47 |

While the invention has been described and illustrated herein by references to various specific material, procedures, and examples, it is understood that the invention is not restricted to the particular material, combinations of material, and procedures selected for that purpose. Numerous variations of such details can be implied and will be appreciated by those skilled in the art.

What is claimed is:

1. A medium suitable for the culture of marine bacteria comprising liver digest, salts, and a liquid solvent in amounts sufficient for the growth and maintenance of marine bacteria.

2. The medium of claim 1 wherein the liver is porcine, bovine, or ovine.

3. The culture medium of claim 1, wherein the salts are NaCl, MgCl•6H$_2$O, Na$_2$SO$_4$, NaHCO$_3$, KBr, H$_3$BO$_3$, SrCl$_3$, NaSiO$_3$•9H$_2$O, NH$_4$NO$_3$, and FeCl$_3$500 6H$_2$O.

4. The culture medium of claim 3 which further comprises a salt selected from the group consisting of KH$_2$PO$_4$ and K$_2$HPO$_4$.

5. The culture medium of claim 3 which further comprises KH$_2$PO$_4$ and K$_2$HPO$_4$.

6. A medium suitable for the large-scale culture of marine bacteria comprising 3% w/v porcine liver digest, 80 g/l NaCl, 8.8 g/l MgCl•6H$_2$O, 3.14 g/l Na$_2$SO$_4$, 0.16 g/l NaHCO$_3$, 0.01–0.20 g/l KBr, 0.02 g/l H$_3$BO$_3$, 0.03 g/l SrCl$_3$, 0.01 g/l NaSiO$_3$•9H$_2$O, 0.05 g/l NH$_4$NO$_3$, and 0.05 g/l FeCl$_3$•6H$_2$O, dissolved in distilled water and adjusted to pH 7.5.

7. The medium of claim 6 which further comprises 13.6 g/l KH$_2$PO$_4$ or 21.3 g/l K$_2$HPO$_4$.

8. The medium of claim 6 which further comprises 13.6 g/l KH$_2$PO$_4$ and 21.3 g/l K$_2$HPO$_4$.

9. A method of large scale fermentation of marine bacteria comprising inoculating marine bacteria into the medium of claim 1 and incubating said bacteria.

* * * * *